United States Patent [19]

Beckett et al.

[11] Patent Number: 6,042,698

[45] Date of Patent: Mar. 28, 2000

[54] DECOLORIZATION PROCESS

[75] Inventors: David Robert Beckett, Hessle; Russell James Milner, Thorngumbald, both of United Kingdom

[73] Assignee: BP Chemicals Limited, London, United Kingdom

[21] Appl. No.: 09/120,122

[22] Filed: Jul. 22, 1998

[30] Foreign Application Priority Data

Jul. 22, 1997 [GB] United Kingdom .................. 9715318

[51] Int. Cl.$^7$ ........................... C07B 63/00; C07C 45/00
[52] U.S. Cl. ...................... 204/158.21; 568/366
[58] Field of Search ....................... 204/158.21; 568/366

[56] References Cited

U.S. PATENT DOCUMENTS

| | | | |
|---|---|---|---|
| 4,248,673 | 2/1981 | Cheminal et al. | 203/35 |
| 4,434,301 | 2/1984 | Papa | 568/366 |
| 4,917,783 | 4/1990 | Yokota et al. | 204/157.15 |
| 5,358,611 | 10/1994 | Bauer, Jr. et al. | 204/157.093 |

FOREIGN PATENT DOCUMENTS

| | | |
|---|---|---|
| 0 759 421 A1 | 2/1997 | European Pat. Off. . |
| 3-005428 | 1/1991 | Japan . |

OTHER PUBLICATIONS

Derwent Publications, No. 91–054738, XP002083318 (1991). No Month Available.

Derwent Publications, No. 87–339782, XP002083319 (1987). No Month Available.

Patent Abs. of Japan, vol. 005, No. 071 (1981), Feb. 1981.

*Primary Examiner*—Edna Wong
*Attorney, Agent, or Firm*—Nixon & Vanderhye

[57] ABSTRACT

The present invention is a process for reducing the color intensity of discolored isophorone, said process comprising exposing the discolored isophorone to UV radiation suitably having a wavelength in the region of about 370–400 nanometers. The decolorization method is advantageous in that the use of 'foreign chemicals' is avoided. Furthermore there are no waste-disposal problems that are encountered with the use of carbon or Fuller's earth.

6 Claims, No Drawings

DECOLORIZATION PROCESS

This invention relates to the decolourisation of isophorone by exposure to ultra-violet (UV) light rays.

Isophorone synthesised by conventional methods eg from acetone is usually discoloured having a greenish tinge. Isophorone is a powerful high-boiling point solvent used in the manufacture of coatings, PVC, chemical intermediates, printing inks and pesticides. Consequently it is desirable to reduce the discolouration of isophorone which in the pure form is yellow and can appear 'distinctly greenish' when it contains high boiling point impurities at levels of up to 100 ppm.

Conventional decolourisation methods typically involve the use of oxidizing ('bleaching') materials, such as hydrogen peroxide or ozone, or some chemical absorbent material such as activated carbon or Fuller's earth. The use of such methods is likely to introduce 'foreign' chemicals into isophorone which may have an adverse effect on some of the end uses of isophorone. Moreover the use of chemical absorbent material may give rise to waste disposal and handling problems.

It has now been found that exposure to ultra-violet radiation significantly reduces the colour intensity of isophorone to such an extent that it appears almost 'water white'.

Accordingly, the present invention is a process for reducing the colour intensity of discoloured isophorone, said process comprising exposing the discoloured isophorone to UV radiation.

The UV radiation source used in the process can be an artificial UV source (UV lamp) or sunlight.

The process can be carried out on a large scale by employing commercially available UV treatment cells (commonly used in water purification plants) and circulating isophorone through the UV cells with a residence (irradiation) time sufficient to bring about the desired degree of colour reduction. The wavelength of the UV radiation used is suitably in the region of about 370–400 nanometers, preferably about 380–395 nanometers.

The exposure of discoloured isophorone to UV radiation may be carried out in two ways. The discoloured isophorone may be exposed to the desired amount of UV radiation either in a single pass through the appropriate apparatus (the so-called "once-through" system) or it may be exposed to the desired amount of radiation through multiple short passes through the appropriate apparatus (the so-called "batch circulation" system). Alternatively, a bath of discoloured isophorone can be agitated within a vessel provided with a suitable source of UV light either at the top or on the side of such a vessel.

The decolourisation method is advantageous in that the use of 'foreign chemicals' (which could have a detrimental effect on the manufacturing process) is avoided. Furthermore there are no waste-disposal problems that are encountered with the use of carbon or Fuller's earth.

The present invention is further illustrated with reference to the following Examples:

EXAMPLE 1

Isophorone (3,5,5 tri-methyl-2-cyclohexene-1-one) with an initial green colouration, recording a value of 70 Hazen Units (HU), was passed through a glass flow cell irradiated by a bank of UVA tubes (at least a proportion of the source of radiation used emitting radiation having a wavelength in the region of 370–400 nm such that the sample of isophorone in said cell received 5 minutes of exposure to the radiation. The colour of the irradiated isophorone emerging from the cell was found to have been reduced at least to 10 HU.

To ascertain whether the effects of the UV radiation were permanent, the irradiated sample was placed in a dark room for a period of weeks. There was no return of the colouration.

EXAMPLE 2

16 liters of discoloured isophorone with an initial value of 60 Hazen Units (HU), was stirred in a vessel above which was positioned a bank of UVA tubes used in Example 1 above. After 20 minutes, the colour of the irradiated isophorone found to have a value of 25 HU and after 40 minutes to a value of 15 HU.

A sample of the irradiated isophorone was then placed in a dark room for a period of weeks. There was no return of the colouration

EXAMPLE 3

A sample of discoloured isophorone with an initial value of 70 Hazen Units (HU) was placed in direct sunlight for a continuous period of 30 min. The isophorone was then removed and the colour intensity measured. This resulted in a reduction in colour intensity to a value of 7.5 HU.

The irradiated sample was then placed in a dark room for a period of weeks. There was no return of the colouration.

In all the experiments no detrimental effect was observed in the properties of the treated isophorone or the isophorone content of the decolourised product.

We claim:

1. A process for reducing the colour intensity of discoloured isophorone, said process comprising exposing the discoloured isophorone to UV radiation.

2. A process according to claim 1 wherein the UV radiation used has a wavelength in the region of about 370–400 nanometers.

3. A process according to claim 2 wherein the UV radiation used has a wavelength in the region of about 380–395 nanometers.

4. A process according to claim 1 wherein the UV radiation used in the process is sourced from an artificial UV source or sunlight.

5. A process according to claim 1 wherein the process is carried out by circulating said isophorone through UV cells with a residence time sufficient to bring about the desired degree of colour reduction.

6. A process according to claim 1 wherein the discoloured isophorone is exposed to UV radiation either in a single pass or in multiple short passes.

* * * * *